United States Patent [19]

Sasse et al.

[11] Patent Number: 5,217,795
[45] Date of Patent: Jun. 8, 1993

[54] POLYMERIC WEB COMPOSITIONS HAVING IMPROVED ALKALINE SOLUBILITY FOR USE AS FIBERS

[75] Inventors: Philip A. Sasse, Alpharetta; Debra H. Durrance, Lilburn, both of Ga.; Glenn A. Taylor, Obergerlafingen, Switzerland

[73] Assignee: Kimberly-Clark Corporation, Neenah, Wis.

[21] Appl. No.: 744,136

[22] Filed: Aug. 13, 1991

[51] Int. Cl.$^5$ ............................................... D03D 3/00
[52] U.S. Cl. ..................................... 428/224; 428/284; 428/286; 428/288; 428/296; 428/903; 428/913; 604/358
[58] Field of Search ............... 428/224, 288, 284, 913, 428/296, 903, 286; 604/358

[56] References Cited

U.S. PATENT DOCUMENTS

| | | | |
|---|---|---|---|
| 4,238,582 | 12/1980 | Deleens et al. | 525/430 |
| 4,331,786 | 5/1982 | Foy et al. | 525/408 |
| 5,063,272 | 11/1991 | Sasse | 524/377 |

*Primary Examiner*—James J. Bell
*Attorney, Agent, or Firm*—Gregory E. Croft

[57] ABSTRACT

The properties of (meth)acrylic ester/(meth)acrylic acid copolymer webs, such as films and nonwovens, are improved by blending the ester/acid copolymer with a modified polyolefin, such as an ethylene/(meth)acrylic acid copolymer and/or a styrene/butadiene block copolymer, and a polyether block amide copolymer. The copolymer blend provides a polymeric material which is useful for making personal care products such as diapers and feminine pads in that it can be made water-soluble in alkaline solutions while exhibiting other properties which are necessary for adequate product performance. Such materials are also useful for packaging products, such as film for plastic bags and the like.

34 Claims, No Drawings

POLYMERIC WEB COMPOSITIONS HAVING IMPROVED ALKALINE SOLUBILITY FOR USE AS FIBERS

BACKGROUND OF THE INVENTION

In the production of personal care products, a number of different components and materials are required to construct the products. In the case of diaper manufacture, for example, these components include a backing material, which is typically a film, and an inner liner, which is typically a nonwoven web. Also, composite structures of synthetic and natural fibers have utility as absorbent media in a variety of personal care products. These various synthetic components are typically made from thermoplastic polymers such as polyethylene or polypropylene. However, with a greater emphasis being placed on protecting the environment today, there is a need to develop materials which are more compatible with existing and developing waste disposal technologies while still delivering the performance consumers have come to expect.

Copolymers of (meth)acrylate esters and (meth)acrylic acid are of environmental interest because of their solubility in alkaline solutions and their compostability due to eventual disintegration upon prolonged exposure to moisture, even though they are relatively hydrophobic. Unfortunately, the physical properties which make these materials desirable from an environmental standpoint can make them unsuitable for personal care products. In particular, films made from these polymers in contact with synthetic urine for a period greater than one hour will become hydrated, weak and sticky. This is obviously unacceptable for use in diapers, for example. Films made from these polymers also suffer from a lack of toughness and tear resistance. Films and nonwovens made from these copolymers are somewhat sticky and tend to stick or "block" in roll form. In addition, dimensional stability and aesthetic properties of these materials are also poor.

Therefore there is a need for copolymers of (meth)acrylate esters and (meth)acrylic acid which have modified properties suitable for use as components in personal care products such as diapers, feminine pads, incontinence garments and the like, and packaging products such as film for plastic bags and the like.

SUMMARY OF THE INVENTION

It has now been found that copolymers of (meth)acrylate esters and/or (meth)acrylic acid can be modified with additional materials to provide polymeric webs having improved properties suitable for use in personal care products. More specifically, it has been discovered that modified polyolefins, such as copolymers of ethylene and (meth)acrylic acid and/or block copolymers of styrene and butadiene, and polyether block amide copolymers, when blended with these ester/acid copolymers in controlled ratios, impart increased resistance to moisture for webs made therefrom while retaining the desired selective alkaline solubility. In addition, the tackiness of such webs is decreased, and dimensional stability and had are markedly improved.

Hence, in one aspect, the invention resides in a composition of matter comprising a polymeric blend of three major components, namely: from about 50 to about 90 weight percent, preferably from about 60 to about 90 weight percent, and most preferably from about 70 to about 90 weight percent, of a (meth)acrylate ester/(meth)acrylic acid copolymer; from about 5 to about 30 weight percent, preferably from about 10 to about 15 weight percent, of a modified polyolefin such as a copolymer of ethylene and (meth)acrylic acid and/or a block copolymer of styrene and butadiene; and from about 1 to about 10 weight percent of a polyether block amide copolymer. Because the alkaline solubility of these compositions decreases with increasing amounts of the polyether block amide copolymer and becomes very low at polyether block amide copolymer levels above about 5 weight percent, a preferred composition contains from about 1 to about 5 weight percent, most preferably from about 3 to about 5 weight percent, of the polyether block amide copolymer. However, compositions with greater amounts are still useful for applications requiring disintegration upon prolonged exposure to moisture (e.g. in composting) rather than rapid dissolution in alkaline media.

In another aspect, the invention resides in a polymeric web comprising a blend of from about 50 to about 90 weight percent, preferably from about 60 to about 90 weight percent, and most preferably from about 70 to about 90 weight percent, of a (meth)acrylate ester/(meth)acrylic acid copolymer, from about 5 to about 30 weight percent, preferably from about 10 to about 15 weight percent, of a modified polyolefin such as a copolymer of ethylene and (meth)acrylic acid and/or a block copolymer of styrene and butadiene, and from about 1 to about 10 weight percent, preferably from about 1 to about 5 weight percent, and most preferably from about 3 to about 5 weight percent, of a polyether block amide copolymer. The relative proportions of the three major components will depend upon the desired properties of the product into which they are to be made. For use in making films, for example, it is preferred that the copolymer blend contain from about 50 to about 90 weight percent of an ethyl acrylate/methacrylic acid copolymer or blend of ethyl acrylate/(meth)acrylic acid copolymers, from about 5 to about 15 weight percent of an ethylene/acrylic acid copolymer, and from about 3 to about 8 weight percent of a polyether block amide copolymer. For use in making nonwoven webs, such as spunbonded webs, it is preferred that the copolymer blend contain from about 70 to about 80 weight percent of an ethyl acrylate/methacrylic acid copolymer, from about 8 to about 15 weight percent of a modified polyolefin such as an ethylene/(meth)acrylic acid copolymer and/or a styrene/butadiene block copolymer, and from about 3 to about 5 weight percent of a polyether block amide copolymer.

In a further aspect, the invention resides in an absorbent article having an outer cover, an absorbent core, and an inner liner, wherein any or all of said outer cover, absorbent core and inner liner comprise the webs (nonwoven or film) described herein. Such absorbent articles particularly include diapers and sanitary napkins.

The (meth)acrylate ester/(meth)acrylic acid copolymer serves as the base material for these blends. This base material is preferably solely a pure copolymer, but can be modified with other monomers such as styrene to improve heat and water resistance. Hence for purposes herein, "(meth)acrylate ester/(meth)acrylic acid copolymer" sometimes includes modified (meth)acrylate ester/(meth)acrylic acid copolymers and blends of the pure copolymer with such modified copolymers. One preferred composition comprises ethyl acrylate and methacrylic acid as the major constituents with weight ratios of these two comonomers ranging from about 2:1 to about 4:1 (ester to acid). Another suitable composition comprises copolymers of ethyl acrylate and acrylic acid in the same weight ratio, with a comonomer weight ratio of about 3:1 (ester to acid) being preferred. Still another suitable composition comprises copolymers of methyl acrylate and methacrylic acid, preferably having a comonomer weight ratio of about 4:1 (ester to acid). The ethyl acrylate/methacrylic acid copolymer that is most preferred has a weight ratio of the two comonomers from about 3.5:1 to about 4:1 (ester to acid). the weight average molecular weight of the most preferred ethyl acrylate/methacrylic acid copolymer is about 150,000, with a melt flow rate of about 7 grams per of 10 minutes, as measured at 170° C. using a 2160 g weight and a 2.1 mm by 8 mm capillary. Clearly, however, many similar copolymers can be prepared that will provide similar attributes and can be substituted for the most preferred copolymer in these compositions. For example, any other (meth)acrylate ester derived from an alcohol having from 1 to 18 carbon atoms can be substituted for all or part of the ethyl acrylate. Such substitutions can lead to enhancement of particular properties for specific material applications. Although not limited to one method of manufacture, a method of making such copolymers is described in U.S. Pat. No. 4,870,148 to RB Kunststoffpatent-Verwertugs AG and Belland AG, both of Switzerland, issued Sep. 26, 1989, which is herein incorporated by reference. Such copolymers are commercially available from Belland AG, and the most preferred copolymer is available as product codes GBC 2620 (ethyl acrylate/methacrylic acid copolymer, GBC 2518 (30 weight percent styrene-modified terpolymer), and GBC 1620 (methyl acrylate/methacrylic acid copolymer).

The ethylene/(meth)acrylic acid copolymers to be used as the modified polyolefins of these blends are high melt index dispersible ethylene/acrylic acid copolymers that are typically 20 percent acrylic acid by weight and 300 to 1300 in melt index. They are dispersible in alkaline water without emulsifiers, but are water-resistant in the acid form. Other suitable ethylene/acrylic acid copolymers which are available contain 3 to 9.5 percent acrylic acid by weight and have a melt index from 2.5 to 13.5. Such copolymers are commercially available from Dow Chemical Company, Midland, Mich. under the tradenamde PRIMACOR ®, with the most preferred copolymers being those with product code numbers ranging from 37 5980" to "5990". They are produced by the free radical, high pressure copolymerization of ethylene and acrylic acid in a process similar to that used for producing low-density polyethylene. Also suitable for use in these blends are ethylene/methacrylic acid copolymers. Such copolymers are commercially available from E.I. du Pont, Wilmington, Del., under the tradename NUCREL TM, with grades ranging from 4 to 12 percent methacrylic acid by weight and from 2.5 to 13.5 in melt index.

The styrene/butadiene block copolymers to be used as the modified polyolefin component of these blends are synthetic rubbers typically containing from about 20 to about 40 weight percent styrene and having a melt index of from about 1 to about 20. Specific commercially available materials include CARIFLEX TM TR-1102 or KRATON D-1102 (Shell Chemical Company) and K-Resin KR-02 (British Petroleum Company). Both of these materials provide the same flex properties as the PRIMACOR material described above, but are less soluble and form a hazy blend rather than clear mixture.

The polyether block amide copolymers that are useful in the blends of this invention are thermoplastic elastomers consisting of flexible polyether segments connected with rigid polyamide segments into linear block copolymers. The most suitable polyether block amide copolymers are commercially available from Atochem under the tradename PEBAX TM with grade designations 2533, 3533, 4533 and 5533. Of these grades, the most preferred are the grades designated 2533 and 3533.

In all aspects of this invention, combinations or blends of more than one species within one or more of the three major components can be used to prepare the compositions useful for purposes of this invention and are considered to be equivalents for purposes. Hence for purposes of convenience, unless otherwise specified, any reference to a copolymer is to be interpreted to include one or more copolymers within the particular copolymer genus.

Blends of the three major components can be prepared by mixing the desired weight ratio of the polymer pellets and blending them using any standard equipment commonly used for blending thermoplastic polymers under conditions of heat and high shear. These include the Banbury ® type of intensive production mixer (Farrel Corp. Ansonia, CT) and both single- and twin-screw compounding extruders, which can utilize high-shear mixing screws, co-rotating kneading blocks, etc.

In addition to blends containing the three above-mentioned major components, other components can be added to further enhance the properties of the resulting material. For example, polyethylene glycol can be added to lower the melt viscosity of these copolymers to a range suitable for meltblown or melt sprayed nonwovens and also improve the flexibility of the resulting webs. The amount of polyethylene glycol added to the copolymer blend can be from about 5 to about 20 weight percent, based on the total weight of the final blend, and a preferred range is from about 10 to about 15 weight percent. Suitable polyethylene glycols are available commercially from Union Carbide Corporation, Danbury, Conn., under the tradename CARBOWAX ®; most suitable are product code numbers "3350" and "8000."

Polyethylene can also be added to blends containing the above-mentioned copolymers to improve the softness of the resulting nonwoven webs. The amount of polyethylene added to the copolymer blend can be from about 5 to about 15 weight percent, based on the total weight of the blend. The polyethylene grade must be selected so that the final blend has a melt index suitable for the nonwoven process to be used. Suitable fiber grade polyethylenes are available commercially from Dow Chemical Company, Midland, Mich., under the tradename ASPUN TM, Product code number "6811" is most suitable for blends for spunbound nonwovens and product code numbers "6806" and "6814" are most suitable for blends for meltblown or melt sprayed nonwovens.

Still further improvements to the properties of the webs of this invention, particularly films, can be made by adding certain fillers such as fumed silica, calcium carbonate or talc. Various particulate fillers have been shown to reduce blocking, noise and gloss in the films. Such materials can be added in amounts of from about 2 percent to about 20 weight percent, based on the total weight of the blend. Processing characteristics of the blends for both films and nonwovens can be improved by the incorporation of lubricants or slip agents into the blends. Additives of other types normally used in polymer blends can also be incorporated to provide specific properties as needed, such as antistatic agents, pigments or other colorants, and the like. All of these additive types are generally used in small amounts, usually less than 5 percent.

Films of the copolymer blends can be prepared by extrusion of the blend through a linear film die, allowing the film to attenuate under its own weight into a nip between two rolls (cast film). Alternatively, an annular die can be used to produce a polymeric tube, which can be attenuated by an air stream to form a film "bubble" (blown film).

Nonwoven webs of the copolymer blends can be prepared by extrusion of the blend through a plurality of capillaries, producing a series of filaments. These filaments can be quenched and then attenuated into fibers by an accelerating gas stream. The fibers can be collected on a moving surface, where they are deposited by the gas stream in a random fashion. Passing the resulting batt through a pair of heated rolls bonds the fibers together into an integral web. Alternatively, a hot gas stream may be used to attenuate and break the filaments in the molten state. These discontinuous fibers can be collected on a moving surface, where they will lay down in a random, entangled manner, producing an integral web. Suitable nonwoven webs include, without limitation, meltblown webs, spunbonded webs, and coform webs (meltblown webs in which a second fiber source, such as cellulose fibers, is blown into the primary meltblown fiber stream prior to deposition onto the collecting surface). All of such webs are known in the nonwovens art.

EXAMPLES

Example 1: Preparation of Copolymer Blend

A blend in accordance with this invention was prepared containing 80 percent by weight of Belland's copolymer material designated GBC 2620 AC. This material is reported to be a copolymer of ethyl acrylate and methacrylic acid in a ratio of 4:1 by weight, respectively, containing 1 percent by weight of an antioxidant (Ciba Geigy, Irganox 1076, octadecyl 3-(3,5-di-t-butyl-4-hydroxyphenyl) propionate) and 3 percent by weight of Hostalube TM FA-1 (Hoescht Celanese, mixed amide of ethylenediamine weight of Hostalube TM FA-1 (Hoescht Celanese, mixed amide of ethylenediamine with palmitic and stearic acids). This material was compounded with 11 percent by weight of Primacor ® 5981 (Dow, ethylene-acrylic acid copolymer), 5 percent by weight of PEBAX 2533SA, 2 percent by weight of titanium dioxide pigment, and 2 percent by weight of erucamide as a slip agent.

The ingredients were first mixed thoroughly by means of a drum tumbler, and then transferred to an AccuRate° volumetric feeder. The mixture was metered into a Werner & Pfleiderer 30-mm twin-screw compound extruder for blending. Extruder zones 1 through 6 were set with the following temperature profile (in °C): 100, 101, 110, 121, 140, 145; with the lowest temperature being at the feed zone adjacent to the throat of the extruder where the mixture enters and the highest temperature being at the die from which the molten blend exits.

The extruder screw configuration used was a vented, two-stage mixing screw combination of a type typically used for preparing polyolefin blends. Extruder throughput was maintained at ca. 50 pounds/hour. The molten blend was taken off from a four-strand die into a water bath with a dip length of six feet, then through two air knives to remove as much water as possible. The pellets were ejected from a rotating-knife pelletizer directly into a spin dryer to remove the remaining surface moisture before screening and packaging.

Example 2: Preparation of Copolymer Blend Film

A copolymer blend containing 73 weight percent GBC 2620 WB (the WB grade contains titanium dioxide pigment), 10 weight percent Primacor ® 5990, 5 weight percent PEBAX, 2 weight percent erucamide, and 10% talc was blended as in Example 1. The polymer blend was then processed at a rate of 115 pounds/hour through a single-screw extruder with a 3.5 inch diameter, internally-cooled screw (3:1 compression ratio, 24:1 L/D). A flat temperature profile of 260° F. was used in all extruder zones, transfer piping and in the film die. Film was produced using a six-inch diameter annular die with a die gap of 0.042 inches. A bubble was generated with a diameter of 14–18 inches, producing film that varied from 0.0011 to 0.0014 inches in gauge.

Ultimate tensile strengths were determined to be 1356 grams/inch at 255% elongation (machine direction) and 1000 grams/inch at 285% elongation (cross direction). A similarly-prepared film of 100% GBC 2620 WB with the same gauge of 0.0011 inch had ultimate tensile strengths of 2647 grams/inch at 224% elongation (machine direction) and 1274 grams/inch at 365% elongation (cross direction). The films prepared from the described blend show less isotropy, less tendency to block, better moisture resistance, and better tear resistance than the film prepared from GBC 2620 WB alone.

Example 3: Preparation of Copolymer Blend Nonwoven Web

A copolymer blend of this invention was prepared as described in Example 1. A nonwoven web was prepared from this blend by means of a spunbond process. The polymer blend pellets were introduced into a single-screw extruder having a screw configuration of a type normally used for extrusion of polyolefins. The molten polymer, at a melt temperature of 340° F., was conveyed from the extruder through a metering pump to a fiber-spinning die. Molten polymer strands exiting the die were quenched, attenuated and formed into a web by controlled streams of high-velocity air. The resulting web was carried by a forming wire through compaction and bonding sections to form a point-bonded spunbond nonwoven.

Webs formed in this manner are dimensionally stable (less than 5% shrinkage) and possess acceptable drape, flexibility and softness. Webs prepared by the same process from GBC 2620 with no additives suffered severe shrinkage (up to 50%), distortion, and increasing rigidity over several weeks. Moisture was found to accelerate these changes.

It will be appreciated by those skilled in the art that the foregoing examples, given for purposes of illustration, are not to be construed as limiting the scope of this invention, which includes all equivalents thereto.

We claim:

1. A polymeric web if fibers, said fibers comprising a blend of from about 50 to about 90 weight percent of a copolymer of a (meth)acrylate ester and (meth)acrylic acid, and from about 5 to about 30 weight percent of a copolymer of ethylene and (meth)acrylic acid, and from about 1 to about 10 weight percent of a polyether block amide copolymer.

2. The web of claim 1 wherein the amount of the polyether block amide copolymer is from about 1 to about 5 weight percent.

3. The web of claim 1 wherein the amount of the polyether block amide copolymer is from about 3 to about 5 weight percent.

4. The web of claim 1 wherein said fibers comprise from about 5 to about 15 weight percent polyethylene.

5. The web of claim 1 wherein the (meth)acrylate ester is ethyl acrylate.

6. The web of claim 5 wherein the (meth)acrylic acid of the ethyl acrylate/(meth)acrylic acid copolymer is methacrylic acid.

7. The web of claim 6 wherein the (meth)acrylic acid of the copolymer of ethylene and (meth)acrylic acid is acrylic acid.

8. The web of claim 7 wherein the copolymer of ethyl acrylate and methacrylic acid comprises about 80 weight percent ethyl acrylate moieties and about 20 weight percent methacrylic acid moieties.

9. The web of claim 7 wherein the copolymer of ethylene and acrylic acid comprises about 80 weight percent ethylene moieties and about 20 weight percent acrylic acid moieties.

10. The web of claim 8 wherein said fibers comprise from about 70 to about 90 weight percent of a copolymer of ethyl acrylate and methacrylic acid, from about 10 to about 15 weight percent of a copolymer of ethylene and (meth)acrylic acid, and from about 3 to about 5 weight percent of a polyether block amide copolymer.

11. The web of claim 7 wherein said fibers comprise from about 60 to about 90 weight percent of a copolymer of ethyl acrylate and methacrylic acid, from about 5 to about 10 weight percent of a copolymer of ethylene and (meth)acrylic acid, and from about 3 to about 5 weight percent of a polyether block amide copolymer.

12. A nonwoven web of fibers, said fibers comprising a blend of from about 70 to about 90 weight percent of a copolymer of ethyl acrylate and methacrylic acid, from about 10 to about 15 weight percent of a copolymer of ethylene and (meth)acrylic acid, and from about 3 to about 5 weight percent of a polyether block amide copolymer, wherein said copolymer of ethyl acrylate and methacrylic acid comprises about 80 weight percent ethyl acrylate moieties and about 10 weight percent methacrylic acid moieties and wherein said copolymer of ethylene and acrylic acid comprises about 80 weight percent ethylene moieties and about 20 weight percent acrylic acid moieties.

13. The nonwoven web of claim 12 wherein said fibers comprise from about 5 to about 15 weight percent polyethylene.

14. The nonwoven web of claim 12 wherein said fibers comprise a blend of from about 70 to about 80 weight percent of a copolymer of ethyl acrylate and methacrylic acid and from about 10 to about 15 weight percent of a copolymer of ethylene and acrylic acid.

15. The nonwoven web of claim 12 wherein said fibers comprise from about 5 to about 20 weight percent of polyethylene glycol.

16. The nonwoven web of claim 12 wherein said fibers comprise from about 10 to about 15 weight percent of polyethylene glycol.

17. The nonwoven web of claim 12 wherein said fibers comprise a blend of about 80 weight percent of the copolymer of ethyl acrylate and methacrylic acid, about 10 weight percent of the copolymer of ethylene and acrylic acid, and about 10 weight percent polyethylene glycol.

18. The nonwoven web of claim 12 wherein said fibers comprise from about 5 to about 15 weight percent polycaprolactone.

19. The nonwoven web of claim 12 wherein said web is a meltblown web.

20. The nonwoven web of claim 12 wherein said web is a spunbonded web.

21. The nonwoven web of claim 12 wherein said web is a coform web.

22. An absorbent article comprising an outer cover, an absorbent core and an inner liner, wherein either of said outer cover or said inner liner is a nonwoven web of fibers, said fibers comprising a blend of from about 50 to about 90 weight percent of a copolyemr of a (meth)acrylate ester and (meth)acrylic acid, from about 5 to about 30 weight percent of a copolymer of ethylene and (meth)acrylic acid, and from about 1 to about 10 weight percent of a polyether block amide copolymer.

23. The article of claim 22 wherein the amount of the polyether block amide copolymer is from about 1 to about 5 weight percent.

24. The article of claim 22 wherein the amount of the polyether block amide copolymer is from about 3 to about 5 weight percent.

25. The article of claim 22 wherein said blend further comprises from about 5 to about 15 weight percent polyethylene.

26. The article of claim 22 wherein the (meth)acrylate ester is ethyl acrylate.

27. The article of claim 26 wherein the (meth)acrylic acid of the ethyl acrylate/(meth)acrylic acid copolymer is methacrylic acid.

28. The article of claim 27 wherein the (meth)acrylic acid of the ethylene/(meth)acrylic acid copolymer is acrylic acid.

29. The article of claim 28 wherein the copolymer of ethyl acrylate and methacrylic acid comprises about 80 weight percent ethyl acrylate moieties and about 20 weight percent methacrylic acid moieties.

30. The article of claim 28 wherein the copolymer of ethylene and acrylic acid comprises about 80 weight percent ethylene moieties and about 20 weight percent acrylic acid moieties.

31. The article of claim 28 wherein said fibers comprise about 70 to about 90 weight percent of a copolymer of ethyl acrylate and methacrylic acid and from about 10 to about 15 weight percent of copolymer of ethylene and acrylic acid.

32. The article of claim 28 wherein said fibers comprise from about 80 to about 90 weight percent of a copolymer of ethyl acrylate and methacrylic acid and from about 10 to about 20 weight percent of a copolymer of ethylene and acrylic acid.

33. The absorbent article of claim 22, wherein said absorbent article is a diaper.

34. The absorbent article of claim 22, wherein said absorbent article is a sanitary napkin.

* * * * *

UNITED STATES PATENT AND TRADEMARK OFFICE
CERTIFICATE OF CORRECTION

PATENT NO. : 5,217,795
DATED : June 8, 1993
INVENTOR(S) : P. A. Sasse et al.

It is certified that error appears in the above-identified patent and that said Letters Patent is hereby corrected as shown below:

Column 1, line 62, delete "had" and substitute therefor --hand--.

Column 3, line 13, delete "the" and substitute therefor --The--.

Column 3, line 16, delete "of".

Column 3, line 48, delete "tradenamde" and substitute therefor --tradename--.

Column 3, line 50, delete "37".

Column 5, line 64, delete "compound" and substitute therefor --compounding--.

Col. 7, claim 1, line 1, delete "if" and substitute therefor --of--

Col. 7, claim 10, line 32, delete "8" and substitute therefor --7--

Col. 8, claim 31, line 56, add --a-- between "of" and "copolymer"

Signed and Sealed this

Third Day of May, 1994

Attest:

BRUCE LEHMAN

Attesting Officer    Commissioner of Patents and Trademarks